United States Patent
Takamori et al.

(10) Patent No.: US 10,120,046 B2
(45) Date of Patent: Nov. 6, 2018

(54) MAGNETIC RESONANCE IMAGING APPARATUS

(71) Applicant: Toshiba Medical Systems Corporation, Otawara-shi (JP)

(72) Inventors: Hiromitsu Takamori, Otawara (JP); Kota Watanabe, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 333 days.

(21) Appl. No.: 15/000,274

(22) Filed: Jan. 19, 2016

(65) Prior Publication Data

US 2016/0216349 A1 Jul. 28, 2016

(30) Foreign Application Priority Data

Jan. 28, 2015 (JP) .................................. 2015-014766

(51) Int. Cl.
*G01R 33/385* (2006.01)
*A61B 5/055* (2006.01)
*G01R 33/38* (2006.01)

(52) U.S. Cl.
CPC ........ *G01R 33/3854* (2013.01); *A61B 5/0555* (2013.01); *G01R 33/3802* (2013.01)

(58) Field of Classification Search
CPC ............ G01R 33/3802; G01R 33/3854; A61B 5/0555

See application file for complete search history.

(56) References Cited

U.S. PATENT DOCUMENTS

| 5,635,839 | A | * | 6/1997 | Srivastava | ......... G01R 33/3873 324/318 |
| 6,404,200 | B1 | | 6/2002 | Dietz et al. | |
| 7,375,518 | B2 | * | 5/2008 | Kurome | ............ G01R 33/3806 324/307 |
| 8,710,842 | B2 | * | 4/2014 | Saha | .................. G01R 33/3854 324/318 |
| 2013/0314089 | A1 | | 11/2013 | Katsunuma et al. | |

(Continued)

FOREIGN PATENT DOCUMENTS

| JP | 4-15903 | 2/1992 |
| JP | 2001-104285 | 4/2001 |
| JP | 2009-28259 | 2/2009 |

(Continued)

OTHER PUBLICATIONS

Japanese Office Action dated Sep. 4, 2018 in Japanese Application No. 2015-014766, 4 pages.

*Primary Examiner* — Gregory H Curran
(74) *Attorney, Agent, or Firm* — Oblon, McClelland, Maier & Neustadt, L.L.P.

(57) ABSTRACT

A magnetic resonance imaging apparatus according to an embodiment includes a magnetostatic field magnet, a gradient coil, and a bore tube. The magnetostatic field magnet is formed to have a cylindrical shape. The gradient coil is formed to have a cylindrical shape, on the inside of the magnetostatic field magnet. The bore tube is formed to have a cylindrical shape, on the inside of the gradient coil. A first space between the gradient coil and the bore tube is configured to be kept in a vacuum state while a second space between the gradient coil and the magnetostatic field magnet is configured to be kept in a state not being a vacuum.

16 Claims, 10 Drawing Sheets

(56) References Cited

U.S. PATENT DOCUMENTS

2015/0061677 A1     3/2015  Tsujita et al.

FOREIGN PATENT DOCUMENTS

| JP | 2011-78501 | 4/2011 |
| JP | 2012-157693 | 8/2012 |
| JP | 2012-183309 | 9/2012 |
| JP | 2013-233354 | 11/2013 |
| JP | 2014-18239 | 2/2014 |
| WO | WO 2006/062028 A1 | 6/2006 |

* cited by examiner

MAGNETIC RESONANCE IMAGING APPARATUS

CROSS-REFERENCE TO RELATED APPLICATIONS

This application is based upon and claims the benefit of priority from Japanese Patent Application No. 2015-014766, filed on Jan. 28, 2015; the entire contents of which are incorporated herein by reference.

FIELD

Embodiments described herein relate generally to a magnetic resonance imaging apparatus.

BACKGROUND

Conventionally, as a measure for noise that occurs during an image taking process performed by a magnetic resonance imaging apparatus, a noise reduction technique is known by which sound that propagates to the vicinity of the ears of a patient (i.e., an examined subject) is reduced by bringing the space in the surroundings of a gradient coil, which is a source of the sound, into a vacuum state. As an example of this kind of noise reduction technique, a method is known by which, for instance, the gradient coil is arranged in a hermetically-sealed container, so that the space inside the hermetically-sealed container is brought into a vacuum state.

DETAILED DESCRIPTION

A magnetic resonance imaging apparatus according to an embodiment includes a magnetostatic field magnet, a gradient coil, and a bore tube. The magnetostatic field magnet is formed to have a cylindrical shape. The gradient coil is formed to have a cylindrical shape, on the inside of the magnetostatic field magnet. The bore tube is formed to have a cylindrical shape, on the inside of the gradient coil. A first space between the gradient coil and the bore tube is configured to be kept in a vacuum state while a second space between the gradient coil and the magnetostatic field magnet is configured to be kept in a state not being a vacuum.

Exemplary embodiments of a magnetic resonance imaging apparatus will be explained below, with reference to the accompanying drawings.

First Embodiment

Figure 1:
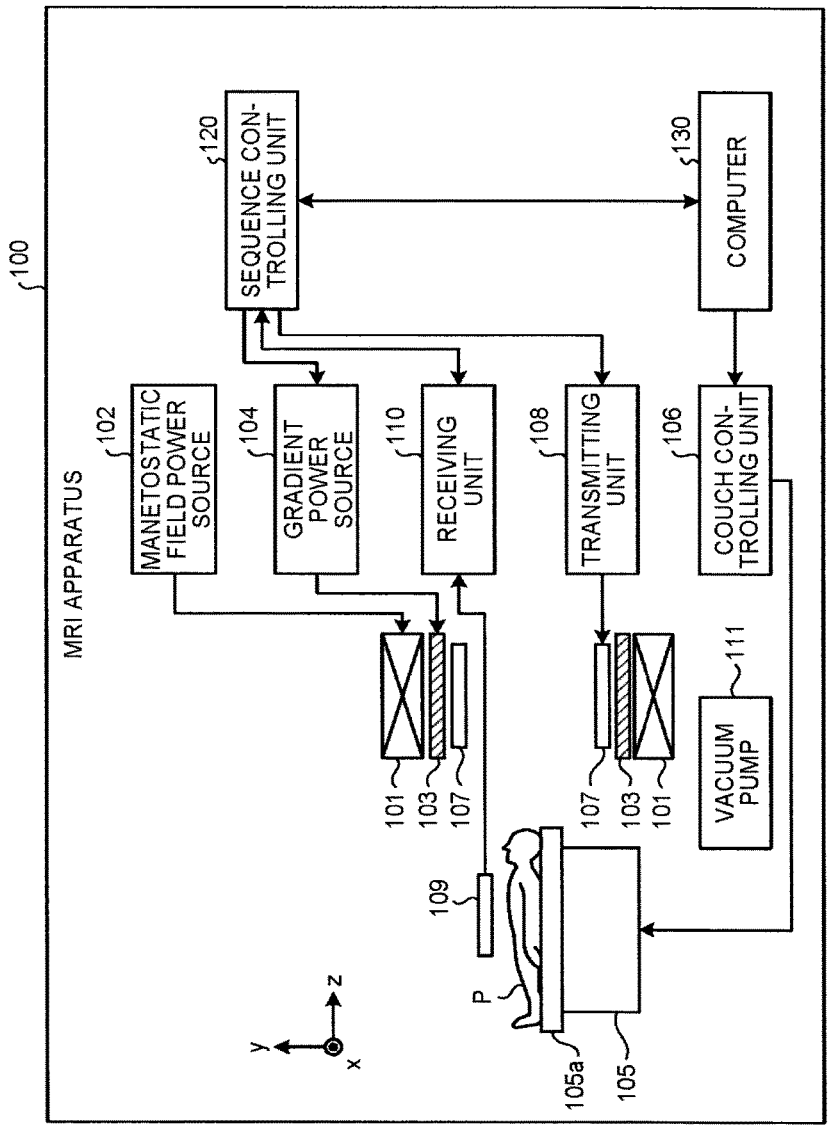
FIG. 1 is a block diagram illustrating a configuration of a Magnetic Resonance Imaging (MRI) apparatus according to a first embodiment.

FIG. 1 is a block diagram illustrating a configuration of a Magnetic Resonance Imaging (MRI) apparatus 100 according to a first embodiment. In the following sections, magnetic resonance imaging apparatuses will be referred to as MRI apparatuses.

As illustrated in FIG. 1, the MRI apparatus 100 includes a magnetostatic field magnet 101, a magnetostatic field power source 102, a gradient coil 103, a gradient power source 104, a couch 105, a couch controlling unit 106, a Whole Body (WB) coil 107, a transmitting unit 108, a reception coil 109, a receiving unit 110, a vacuum pump 111, a sequence controlling unit 120, and a computer 130. In this situation, an examined subject (hereinafter, "patient") P (e.g., a human body) is not included in the MRI apparatus 100. Also, the configuration illustrated in FIG. 1 is merely an example.

The magnetostatic field magnet 101 is a magnet formed to have a substantially hollow circular cylindrical shape and is configured to generate a magnetostatic field in the space on the inside thereof. The magnetostatic field magnet 101 may be configured by using, for example, a superconductive magnet or the like and is configured to be excited by receiving a supply of electric current from the magnetostatic field power source 102. The magnetostatic field power source 102 is configured to supply the electric current to the magnetostatic field magnet 101. Alternatively, the magnetostatic field magnet 101 may be configured by using a permanent magnet. In that situation, the MRI apparatus 100 does not necessarily have to include the magnetostatic field power source 102. Further, the magnetostatic field power source 102 may be provided separately from the MRI apparatus 100. Further, as for the substantially circular cylindrical shape, the circular cylindrical shape may be of a perfect circle or may be distorted so as to have an oval shape, as long as the functions of the MRI apparatus 100 are not significantly impaired. In other words, the magnetostatic field magnet 101 is formed to have a cylindrical shape.

The gradient coil 103 is a coil structure formed to have a substantially hollow circular cylindrical shape and is disposed on the inside of the magnetostatic field magnet 101. The gradient coil 103 is structured by combining three coils corresponding to x-, y-, and z-axes that are orthogonal to one another. By receiving a supply of electric current from the gradient power source 104 individually, the three coils generate gradient magnetic fields of which the magnetic field intensities change along the x-, y-, and z-axes. The gradient magnetic fields along the x-, y-, and z-axes generated by the gradient coil 103 are, for example, a slice-encoding gradient magnetic field $G_{SE}$, (or a slice-selecting gradient magnetic field $G_{SS}$), a phase-encoding gradient magnetic field $G_{PE}$, and a frequency-encoding gradient magnetic field $G_{RO}$. The gradient coil 103 is formed by, for example, impregnating the three coils with epoxy resin, or the like. The gradient power source 104 is configured to supply the electric current to the gradient coil 103. In other words, the gradient coil 103 is formed to have a cylindrical shape, on the inside of the magnetostatic field magnet 101.

The couch 105 includes a couchtop 105a on which the patient P is placed. Under control of the couch controlling unit 106, while the patient P is placed thereon, the couchtop 105a is inserted into the hollow (i.e., an image taking opening) of the gradient coil 103. Normally, the couch 105 is provided so that the longitudinal direction thereof extends parallel to the central axis of the magnetostatic field magnet 101. Under control of the computer 130, the couch controlling unit 106 drives the couch 105 so that the couchtop 105a moves in longitudinal directions and in up-and-down directions.

The WB coil 107 is disposed on the inside of the gradient coil 103 and is configured to generate a radio frequency magnetic field by receiving a supply of a Radio Frequency (RF) pulse from the transmitting unit 108. Also, the WB coil 107 is configured to receive Magnetic Resonance signals (hereinafter "MR signals" as necessary) emitted from the patient P due to an influence of the radio frequency magnetic field and to output the received MR signals to the receiving unit 110.

The transmitting unit 108 is configured to supply the RF pulse corresponding to a Larmor frequency determined by the type of targeted atoms and the magnetic field intensities, to the WB coil 107.

The reception coil 109 is disposed on the inside of the gradient coil 103 and is configured to receive the MR signals emitted from the patient P due to the influence of the radio frequency magnetic field. When having received the MR signals, the reception coil 109 outputs the received MR signals to the receiving unit 110.

The configurations of the WB coil 107 and the reception coil 109 described above are merely examples. For instance, the reception coil 109 does not necessarily have to be provided. Further, the WB coil 107 and the reception coil 109 may be realized by selecting one of the following or combining together two or more of the following: a coil having only a transmitting function; a coil having only a receiving function; and a coil having transmitting and receiving functions.

The receiving unit 110 is configured to detect the MR signals output from the reception coil 109 and to generate MR data on the basis of the detected MR signals. More specifically, the receiving unit 110 generates the MR data by applying a digital conversion to the MR signals output from the reception coil 109. Further, the receiving unit 110 transmits the generated MR data to the sequence controlling unit 120.

The vacuum pump 111 is a pump that brings a predetermined space into a vacuum state, by evacuating the air in the predetermined space. Functions of the vacuum pump 111 in the MRI apparatus 100 will be explained later.

The sequence controlling unit 120 is configured to perform an image taking process on the patient P, by driving the gradient power source 104, the transmitting unit 108, and the receiving unit 110, on the basis of sequence information transmitted from the computer 130. In this situation, the sequence information is information that defines a procedure for performing the image taking process. The sequence information defines: the intensity of the electric current to be supplied to the gradient coil 103 and the timing with which the electric current is to be supplied; the intensity of the RF pulse to be supplied from the transmitting unit 108 to the WB coil 107 and the timing with which the RF pulse is to be applied; the timing with which the MR signals are to be detected by the receiving unit 110, and the like. For example, the sequence controlling unit 120 may be configured with an integrated circuit such as an Application Specific Integrated Circuit (ASIC) or a Field Programmable Gate Array (FPGA), or an electronic circuit such as a Central Processing Unit (CPU) or a Micro Processing Unit (MPU).

When having received the MR signal data from the receiving unit 110 as a result of the image taking process performed on the patient P by controlling the gradient power source 104, the transmitting unit 108, and the receiving unit 110, the sequence controlling unit 120 transfers the received MR signal data to the computer 130.

The computer 130 is configured to exercise overall control of the MRI apparatus 100, to generate MR images, and the like. For example, the computer 130 causes the sequence controlling unit 120 to execute an image taking sequence on the basis of image taking conditions input by the operator. Further, the computer 130 reconstructs images on the basis of the MR signal data transmitted thereto from the sequence controlling unit 120. The computer 130 then causes the reconstructed images to be stored into a storage unit and/or to be displayed by a display unit. The computer 130 may be, for example, an information processing apparatus such as a computer apparatus.

The MRI apparatus 100 according to the first embodiment configured as described above further has a structure described below, for the purpose of reducing noise by using a simple configuration.

Figure 2:
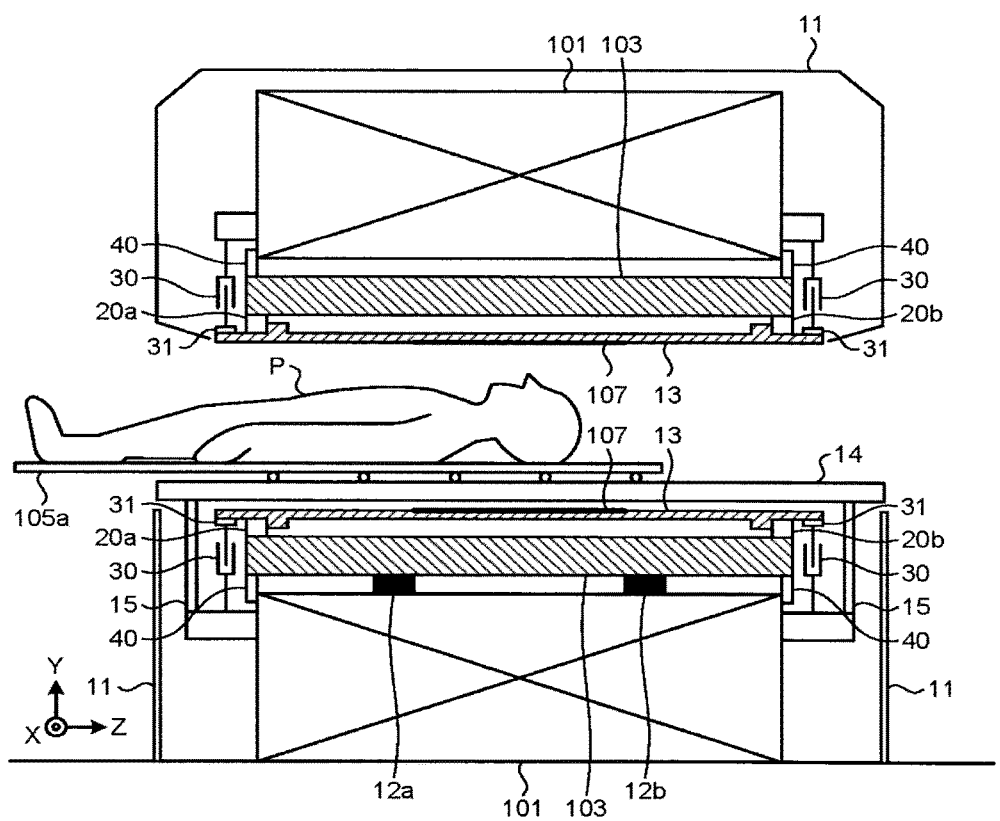
FIG. 2 is a drawing for explaining an internal structure of a gantry of the MRI apparatus according to the first embodiment.

FIG. 2 is a drawing for explaining an internal structure of a gantry of the MRI apparatus 100 according to the first embodiment. FIG. 2 is a cross-sectional view on a y-z plane passing through the central axis of the magnetostatic field magnet 101.

As illustrated in FIG. 2, the gantry is structured, for example, so as to have a substantially circular cylindrical space (a bore) in which the patient P is placed and to be enclosed by a gantry cover 11. The gantry has, on the inside thereof, the magnetostatic field magnet 101 and the gradient coil 103 that are each formed to have the substantially circular cylindrical shape. In this situation, the gradient coil 103 is supported by coil supporting units 12a and 12b within the space formed on the inside of the magnetostatic field magnet 101. The coil supporting units 12a and 12b are formed by using a vibration-isolating material. The coil supporting units 12a and 12b are, for example, formed by using the vibration-isolating material such as rubber or an elastic foam material, in order to support the weight of the gradient coil 103 while reducing vibration thereof.

Further, a bore tube 13 that forms the space (the bore) in which the patient P is placed is disposed in the space formed on the inside of the gradient coil 103. To ensure the strength thereof, the bore tube 13 is formed to have a substantially circular cylindrical shape by performing a filament winding molding process (a FW molding process) while using glass fibers and epoxy resin or polyester resin. Further, the bore tube 13 has the WB coil 107 installed therewith. The bore tube 13 is an example of the bore tube. In other words, the bore tube 13 is formed to have a cylindrical shape, on the inside of the gradient coil 103.

Further, the bore has installed therein a couch rail 14 along which the couchtop 105a moves. The couch rail 14 is supported on the magnetostatic field magnet 101 by a couch rail supporting unit 15.

In this situation, the space formed between the gradient coil 103 and the bore tube 13 is hermetically sealed by annular-shaped vacuum sealing members 20a and 20b and is brought into a vacuum state by, for example, the vacuum pump 111 configured to evacuate the air. Further, the weight of the bore tube 13 is supported on the magnetostatic field magnet 101 by supporting structures 30. A vibration-isolating member 31 is provided between the bore tube 13 and the supporting structures 30. Further, the space formed between the gradient coil 103 and the magnetostatic field magnet 101 is closed by sound-blocking lids 40. The sound-blocking lids 40 do not necessarily have to hermetically seal the space. In this situation, the "vacuum state" includes a low-pressure state approximate to a vacuum state. Further, the vacuum sealing members 20a and 20b do not necessarily have to be annular-shaped. For example, it is sufficient if the vacuum sealing members 20a and 20b are each loop-shaped. In the following sections, in order to distinguish the space formed between the gradient coil 103 and the bore tube 13 and the space formed between the gradient coil 103 and the magnetostatic field magnet 101 from each other, the former may be referred as a "first space", whereas the latter may be referred to as a "second space".

In other words, the first space is the space formed between the gradient coil 103 and the bore tube 13, as a result of arranging the bore tube 13 which has the cylindrical shape and of which the inside diameter is smaller than that of the gradient coil 103 to be disposed on the inside of the gradient coil 103 that has the cylindrical shape. In other words, the first space can be described as a space that has a cylindrical shape and is formed by the inner circumferential surface of the gradient coil 103 and the outer circumferential surface of the bore tube 13. Similarly, the second space can be described as a space that has a cylindrical shape and is formed by the inner circumferential surface of the magnetostatic field magnet 101 and the outer circumferential surface of the gradient coil 103.

As explained above, in the MRI apparatus 100 according to the first embodiment, the hermetically-sealed space between the gradient coil 103 and the bore tube 13 is hermetically sealed and is in the vacuum state. Further, in the MRI apparatus 100, the space between the gradient coil 103 and the magnetostatic field magnet 101 is not hermetically sealed and contains air. In other words, in the MRI apparatus 100, out of the two spaces, namely, the space between the gradient coil 103 and the bore tube 13 and the space between the gradient coil 103 and the magnetostatic field magnet 101, the vacuum pump 111 bring the space between the gradient coil 103 and the bore tube 13 into the vacuum state. In other words, the vacuum pump 111 brings the first space into the vacuum state while the second space is kept in a state not being a vacuum. With this arrangement, the MRI apparatus 100 according to the first embodiment is configured so that it is possible to reduce the noise by using the simple configuration.

For example, sounds arising from the gradient coil 103 can roughly be categorized into air-propagated sounds that propagate to the patient P by using the air in the surroundings of the gradient coil 103 as a medium and solid-propagated sounds that propagate to the patient P by using solids that are in contact with the gradient coil 103 as a medium. The air-propagated sounds can roughly be categorized into sound (hereinafter, "inside air-propagated sound") that propagates from the inside of the gradient coil 103 and sound (hereinafter, "outside air-propagated sound") that propagates from the outside of the gradient coil 103. More specifically, the inside air-propagated sound is sound that propagates by using the air positioned between the gradient coil 103 and the bore tube 13 as a medium, whereas the outside air-propagated sound is sound that propagates by using the air positioned between the gradient coil 103 and the magnetostatic field magnet 101 as a medium.

In this situation, in the MRI apparatus 100 according to the first embodiment, the space formed between the gradient coil 103 and the bore tube 13 is brought into the vacuum state. With this arrangement, the MRI apparatus 100 is configured so that it is possible to efficiently block the inside air-propagated sound.

Further, the outside air-propagated sound primarily leaks to the outside from the end parts in terms of the axial direction and reaches the bore after being diffracted. In that situation, the impact made on the patient P by the outside air-propagated sound is small, because the outside air-propagated sound is weakened due to the long propagation distance and is also blocked by the sound-blocking lids 40, the gantry cover 11, and the like. Further, although the outside air-propagated sound also propagates through vibration of the magnetostatic field magnet 101, the impact made on the patient P via this route is also small. For these reasons, in the MRI apparatus 100 according to the first embodiment, the space formed between the gradient coil 103 and the magnetostatic field magnet 101 is not brought into a vacuum state.

As explained above, the MRI apparatus 100 according to the first embodiment is configured so that the space formed between the gradient coil 103 and the bore tube 13 is in a vacuum state, whereas the space formed between the gradient coil 103 and the magnetostatic field magnet 101 is not in a vacuum state. The MRI apparatus 100 according to the first embodiment therefore requires neither a structure for hermetically sealing the space formed between the gradient coil 103 and the magnetostatic field magnet 101 nor a structure for evacuating the air from the space. Consequently, it is possible to reduce the noise with the simple configuration.

In other words, the first space is the space formed between the gradient coil 103 and the bore tube 13 as a result of arranging the bore tube 13 which has the cylindrical shape and of which the inside diameter is smaller than that of the gradient coil 103 to be disposed on the inside of the gradient coil 103 that has the cylindrical shape. That is to say, the first space can be described as a space that has a cylindrical shape and is formed by the inner circumferential surface of the gradient coil 103 and the outer circumferential surface of the bore tube 13. In this situation, by closing the cylindrical-shaped first space with vacuum sealing members 20 arranged on the two ends in terms of the axial direction, the MRI apparatus 100 according to the first embodiment is able to keep the entirety of the first space hermetically-sealed and in the vacuum state. Consequently, the MRI apparatus 100 according to the first embodiment is configured so that it is possible to effectively reduce the air-propagated sound that propagates from the gradient coil 103 to the patient P, by using the simple configuration.

Further, due to the simple configuration, because the number of component parts used in the MRI apparatus 100 is small, it is easy to assemble the MRI apparatus 100. Further, due to the simple configuration, because the number of locations from which air may leak is kept small in the MRI apparatus 100, it is easy to maintain the vacuum state, and the load on the vacuum pump 111 is therefore kept small. For this reason, it is possible to use an inexpensive vacuum pump as the vacuum pump 111 for the MRI apparatus 100.

The configuration illustrated in FIG. 2 is merely an example. For instance, a bore cover may be installed on the inside of the bore tube 13, for the purpose of adding a design to the inside of the bore or further blocking the sound. In other words, in one example, the bore tube 13 itself may serve as a bore cover. In another example, separately from the bore tube 13, the bore cover may be installed on the inside of the bore tube 13.

The Vacuum Sealing Members 20

Figure 3:
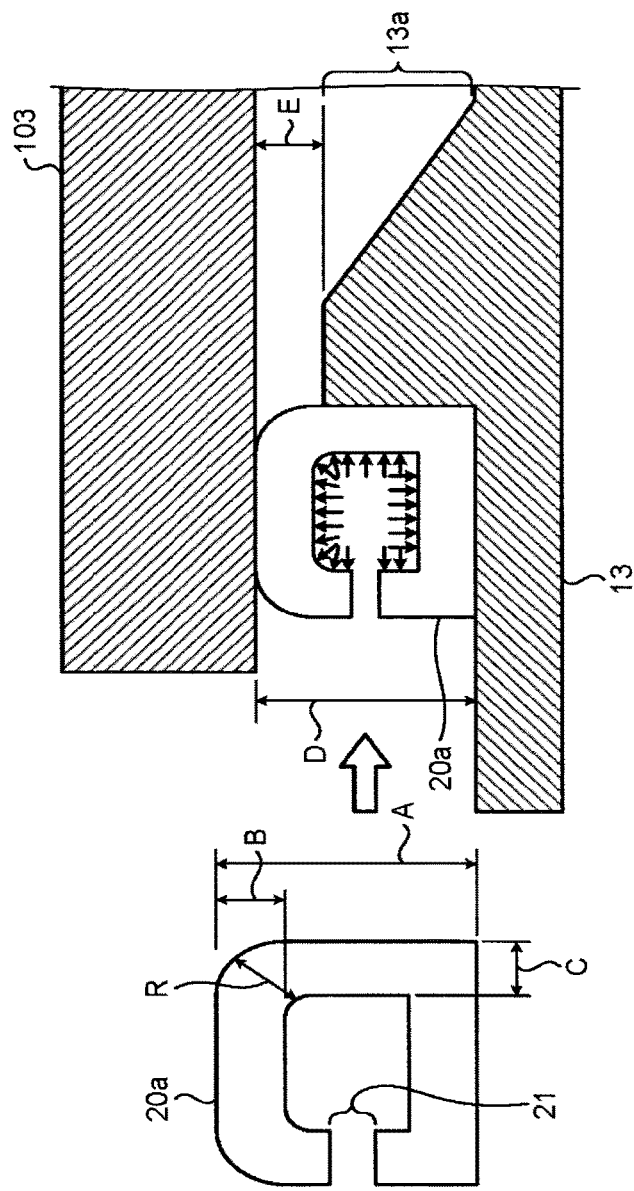
FIG. 3 is a drawing for explaining a structure of a vacuum sealing member according to the first embodiment.
Figure 4:
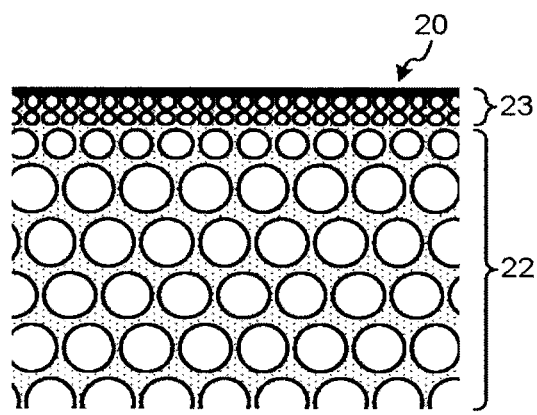
FIG. 4 is another drawing for explaining the structure of the vacuum sealing member according to the first embodiment.
Figure 5:
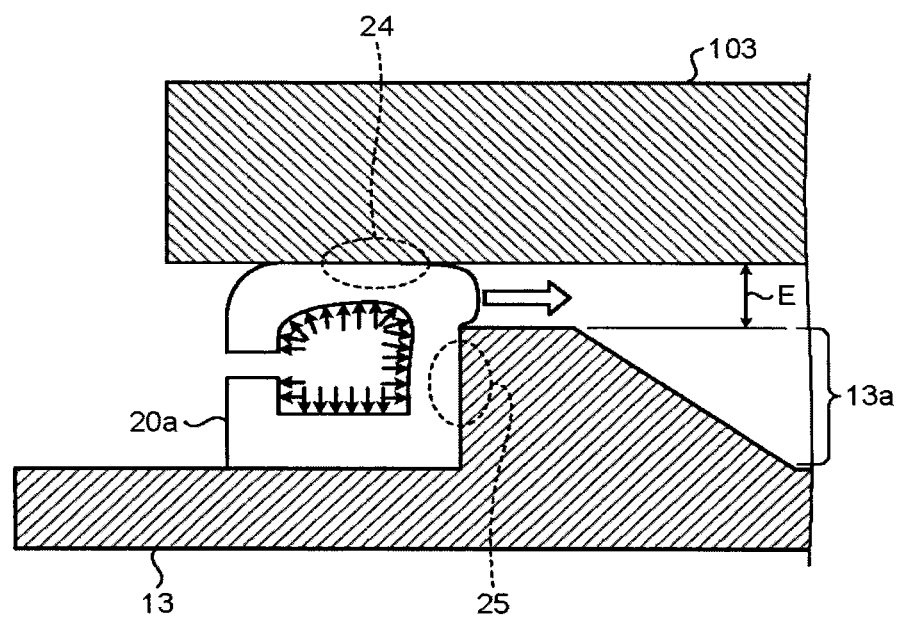
FIG. 5 is yet another drawing for explaining the structure of the vacuum sealing member according to the first embodiment.

FIGS. 3 to 5 are drawings for explaining a structure of the vacuum sealing members 20 according to the first embodiment. FIG. 3 is a cross-sectional view obtained when the vacuum sealing member 20a is inserted between the gradient coil 103 and the bore tube 13. FIG. 4 is an enlarged view of a cross-sectional plane of the vacuum sealing member 20a. FIG. 5 is a cross-sectional view of the vacuum sealing member 20a obtained when the space formed between the gradient coil 103 and the bore tube 13 is brought into a vacuum state. Although the vacuum sealing member 20a will be explained with reference to the drawings in the following sections, because the vacuum sealing members 20a and 20b basically have the same configuration as each other, either of the vacuum sealing members 20a and 20b will be referred to as the "vacuum sealing member 20" without being distinguished from the other.

The vacuum sealing member 20 illustrated in FIG. 3 is, for example, an elastic member obtained by forming a foam material such as chloroprene into an annular shape. The vacuum sealing member 20 is inserted into the space formed between the gradient coil 103 and the bore tube 13 (the arrow in FIG. 3). Further, the bore tube 13 has a projection 13a formed on the outer circumferential surface thereof (the surface that is in contact with the vacuum sealing member 20). In order to keep the space formed between the gradient coil 103 and the bore tube 13, the projection 13a is configured to fix the vacuum sealing member 20 in the vicinity of the end part in terms of the axial direction. With this arrangement, the vacuum sealing member 20 hermetically seals the space formed between the gradient coil 103 and the bore tube 13. Hereinafter, the space that is hermetically sealed may be referred to as "hermetically-sealed space". The projection 13a may be, for example, formed as a part of the bore tube 13 during the forming process of the bore tube 13. Further, the vacuum sealing member 20 is an example of the hermetically-sealing member. In other words, the vacuum sealing member 20 is formed to have the annular shape along the circumferential direction of the gradient coil 103, for the purpose of closing the space formed between the gradient coil 103 and the bore tube 13. More specifically, as for the external appearance thereof, for example, the vacuum sealing member 20 is an annular-shaped elastic member of which the inside diameter is substantially equal to that of the cylindrical-shaped space formed between the gradient coil 103 and the bore tube 13.

Further, the vacuum sealing member 20 is inserted into the space formed between the gradient coil 103 and the bore tube 13 while being squashed. More specifically, the vacuum sealing member 20 is inserted while being squashed in such a manner that a length A (the length from the plane in contact with the gradient coil 103 to the plane in contact with the bore tube 13) becomes equal to a length D (the distance between the gradient coil 103 and the bore tube 13). The squashed leeway (corresponding to the difference between the length A and the length D) is arranged to account for a sufficient length in relation to a displacement amount caused by vibration of the gradient coil 103. With this arrangement, even if the gradient coil 103 vibrates, because the vacuum sealing member 20 changes the form thereof so as to conform to the vibration (shape conformability), it is possible to maintain the hermetically-sealed space.

Further, the vacuum sealing member 20 has an annular-shaped hollow on the inside thereof, and also, has formed therein a hole 21 that reaches the hollow, on the plane positioned opposite the plane positioned on the hermetically-sealed space side. The hole 21 allows air to flow into the hollow of the vacuum sealing member 20. With these arrangements, the atmospheric pressure (approximately 0.1 Mpa) is applied to the surface of the hollow of the vacuum sealing member 20. In this situation, it is sufficient if at least one hole 21 is formed. When a plurality of holes 21 are formed, it is desirable to arrange the holes 21 in a discrete manner along the circumference of the vacuum sealing member 20. Further, the hole 21 does not necessarily have to be a round hole and may be a slit-like hole. Further, the hollow formed on the inside of the vacuum sealing member 20 does not necessarily have to have an annular shape. For example, it is sufficient if the hollow is loop-shaped.

In other words, as illustrated in FIG. 3, the outline of a cross-section of the vacuum sealing member 20 before inserted into the first space is in the shape of a "D" formed by one flat plane and one curved plane. When being inserted into the first space in such a manner that the flat plane section of the "D" shape is in contact with the bore tube 13, the vacuum sealing member 20 is squashed by the gradient coil 103. As a result, the outline of the cross-section of the vacuum sealing member 20 after being inserted into the first space has a shape defined by four planes, namely, the plane in contact with the bore tube 13, the plane in contact with the gradient coil 103, the plane positioned on the hermetically-sealed space side, and the plane positioned opposite the plane positioned on the hermetically-sealed space side. In other words, the hole 21 formed in the plane positioned opposite the plane positioned on the hermetically-sealed space side is formed in the curved plane section of the "D" shape of the vacuum sealing member 20 before the insertion. More specifically, for example, the hole 21 is formed in the curved plane section of the "D" shape so as to extend parallel to the flat plane section of the "D" shape by passing through substantially the center of the cross-sectional plane.

Although not illustrated in FIG. 3, the vacuum sealing member 20 is inserted into the space formed between the gradient coil 103 and the bore tube 13 while vacuum-use silicone grease or the like is applied to the surface thereof. With this arrangement, the vacuum sealing member 20 is able to exhibit a sealing capability, even if the contact surfaces between the vacuum sealing member 20 and the gradient coil 103 and/or the contact surfaces between the vacuum sealing member 20 and the bore tube 13 are rough to some extent. Further, the shape conformability of the vacuum sealing member 20 is also enhanced by applying the vacuum-use silicone grease or the like thereon.

Further, the length B corresponds to the thickness of such a part of the vacuum sealing member 20 that is in contact with the gradient coil 103. The length C corresponds to the thickness of such a part of the vacuum sealing member 20 that is positioned on the hermetically-sealed space side. The length E corresponds to the distance between the upper end of the projection 13a and the inner circumferential surface of the gradient coil 103. The length R corresponds, as explained later, to the thickness of the part that is sucked as a result of bringing the hermetically-sealed space into the vacuum state.

As illustrated in FIG. 4, the vacuum sealing member 20 has a closed-cell foam structure in which the foam cells are independent of one another. With this configuration, the vacuum sealing member 20 is able to prevent air from flowing into the hermetically-sealed space, unlike in another situation with an open-cell foam structure in which the foam cells are continuous.

Further, due to the open-cell foam structure, the vacuum sealing member 20 has flexibility. For this reason, the vacuum sealing members 20 has excellent shape conformability for the vibration of the gradient coil 103. In addition, it is possible to reduce the solid-propagated sound that propagates from the gradient coil 103 by using the vacuum sealing member 20 itself as a medium.

Further, the sizes of the cells in the closed-cell foam structure of the vacuum sealing member 20 are arranged in such a manner that the farther a cell is positioned from the surface (the outer surface of the vacuum sealing member 20 and the surface of the hollow), e.g., in a deeper region 22, the larger the cell is. On the contrary, the closer a cell is positioned to the surface, e.g., in a region 23, the smaller the cell is. Further, the vacuum sealing member 20 has, on the surface thereof, a skin layer in which almost no closed cell is present. With this configuration, the vacuum sealing member 20 has excellent resistance to deterioration of the surface and tearing.

The configuration illustrated in FIG. 4 is merely an example. For instance, as for the closed-cell foam structure mentioned above, all the foam cells in the vacuum sealing member 20 do not necessarily have to be completely closed (i.e., independent). In other words, some of the foam cells in the vacuum sealing member 20 may be open foam cells (i.e., continuous), as long as it is possible to prevent air from flowing into the hermetically-sealed space.

As illustrated in FIG. 5, as a result of bringing the hermetically-sealed space into the vacuum state, the vacuum sealing member 20 is pulled in the direction toward the hermetically-sealed space (in the direction of the outlined arrow) and is thus partially deformed. Generally speaking, when sealing members are deformed, a gap may be created on the contact surface. As for the vacuum sealing member 20, however, because the atmospheric pressure is applied to the surface of the hollow of the vacuum sealing member 20 as explained above, the contact pressure on the contact surface in each of regions 24 and 25 is increased. For this reason, the vacuum sealing member 20 has excellent sealing capability on (ability to keep close contact with) the contact surface in the regions 24 and 25. Thus, even if the vacuum sealing member 20 is pulled in the direction toward the hermetically-sealed space, the deformation is only at such a level that a part of the vacuum sealing member 20 goes into the narrow space formed between the gradient coil 103 and the projection 13a. In addition, the shape conformability of the vacuum sealing member 20 is also improved by the atmospheric pressure applied to the surface of the hollow.

The configuration illustrated in FIG. 5 is merely an example. For instance, in FIG. 5, the length E is approximately equal to the length B and is approximately a quarter of the length D of the hermetically-sealed space. However, possible embodiments are not limited to this example. For instance, the length E may be changed to an arbitrary length, as long as the vacuum sealing member 20 is able to achieve the sealing capability. More specifically, it is acceptable to increase the length E up to approximately a half of the length D, if it is possible to make the vacuum sealing members 20 firmer by changing any of the lengths B, C, and R and/or changing the expansion ratio of the closed-cell foam. On the contrary, it is also acceptable to shorten the length E. However, it is desirable to keep a sufficient distance so that the gradient coil 103 and the projection 13a do not collide with each other even when the gradient coil 103 vibrates.

As explained above, the MRI apparatus 100 according to the first embodiment is configured so that the vacuum sealing members 20 are each formed to have the annular shape and to have the annular-shaped hollow on the inside thereof and to hermetically seal the space formed between the gradient coil 103 and the bore tube 13. On the plane positioned opposite the plane positioned on the hermetically-sealed space side, each of the vacuum sealing members 20 has the hole 21 reaching the hollow. With these arrangements, the vacuum sealing members 20 are able to reduce the inside air-propagated sound by using the simple configuration.

In other words, each of the vacuum sealing members 20 is formed so that the overall external appearance thereof is annular-shaped, and also, the cross-section thereof is annular-shaped. In other words, each of the vacuum sealing members 20 is formed in the shape of a loop having a diameter approximately equal to the diameter of the first space, in order to hermetically seal the first space at the two ends thereof in the axial direction. Further, each of the vacuum sealing members 20 is formed so that the cross-section thereof is also in the shape of a loop, as a result of being formed to have the hollow therein in order to improve the sealing capability with the use of the atmospheric pressure. With these arrangements, the vacuum sealing members 20 are able to reduce the air-propagated sound that propagates through the first space, although the configurations thereof are simple.

For example, when installing the MRI apparatus 100, a person who works on the MRI apparatus 100 is able to form the hermetically-sealed space only by inserting the two vacuum sealing members 20a and 20b from the two ends into the positions between the gradient coil 103 and the bore tube 13. Thus, the MRI apparatus 100 has excellent ease of assembly.

Further, in the MRI apparatus 100, the projection 13a is provided on the inside of the position where each of the vacuum sealing members 20 is installed. With this arrangement, the MRI apparatus 100 is configured so that it is possible to prevent the vacuum sealing members 20 from being sucked into the hermetically-sealed space when the hermetically-sealed space is brought into the vacuum state.

Further, the sizes of the cells in the closed-cell foam structure of the vacuum sealing members 20 in the MRI apparatus 100 are arranged in such a manner that the closer a cell is positioned to the surface of the vacuum sealing members 20, the smaller the cell is. Consequently, the vacuum sealing members 20 are resistant to deterioration and cracking and the like.

The Supporting Structures 30

Figure 6:
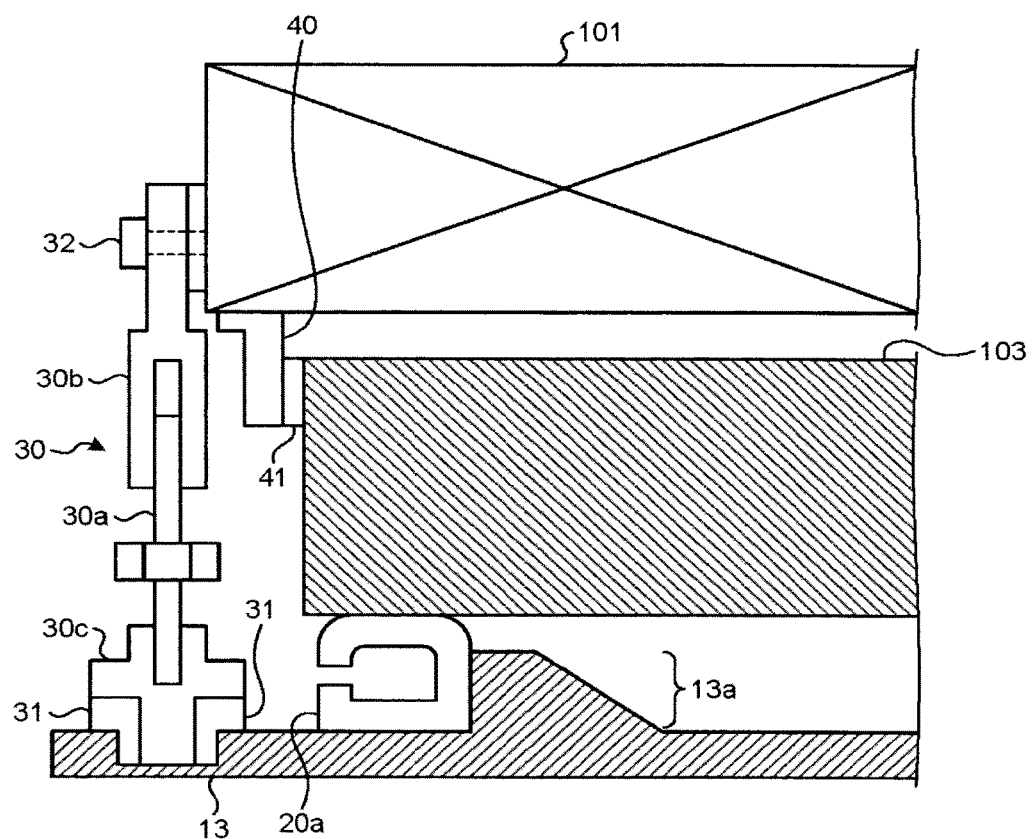
FIG. 6 is a drawing for explaining a structure of a supporting structure according to the first embodiment.
Figure 7:
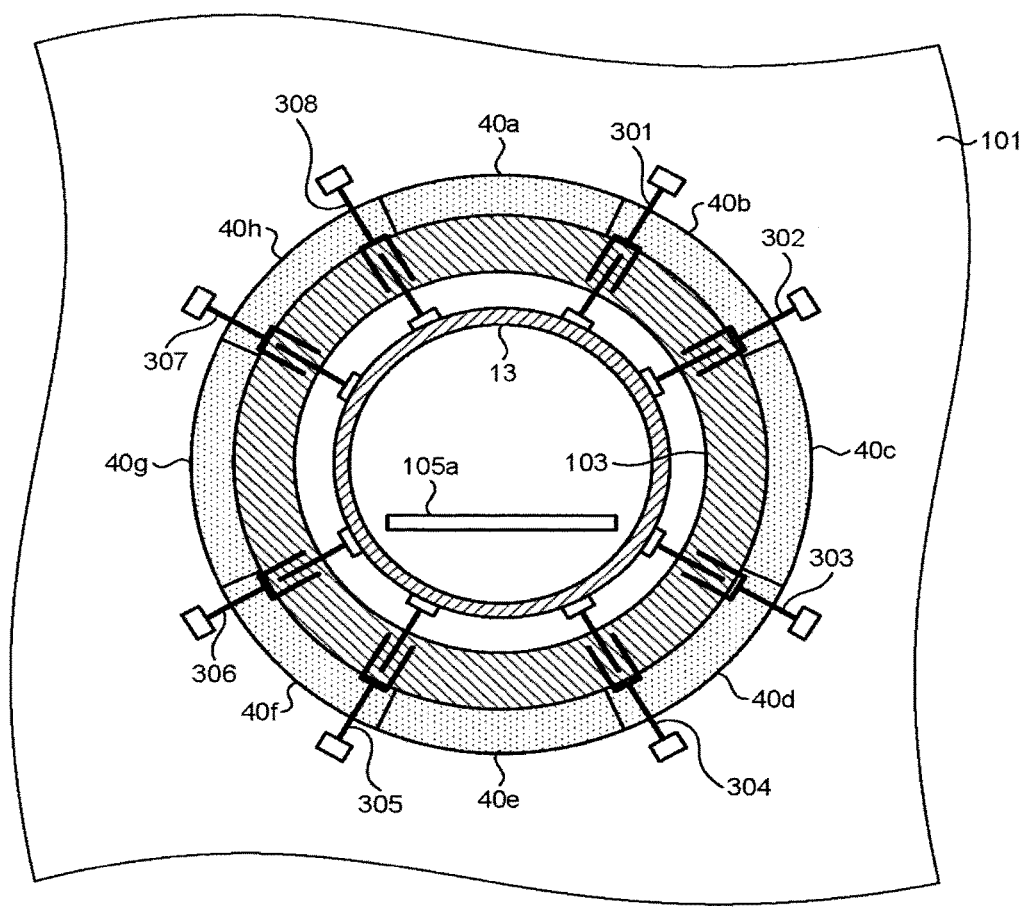
FIG. 7 is another drawing for explaining the structure of supporting structures according to the first embodiment.

FIGS. 6 and 7 are drawings for explaining a structure of one of the supporting structures 30 according to the first embodiment. FIG. 6 is a cross-sectional view of the vacuum sealing member 20 near an installation position of the supporting structure 30. FIG. 7 is a drawing of a structure near an end face of the gradient coil 103, as viewed in the axial direction. Although FIGS. 6 and 7 also illustrate a structure of one of the sound-blocking lids 40, the supporting structures 30 will be explained in the following sections. The sound-blocking lids 40 will be explained later.

As illustrated in FIG. 6, the supporting structure 30 includes a first supporting structure 30a having a male screw thread, a second supporting structure 30b having a female screw thread corresponding to the male screw thread, and a third supporting structure 30c supporting the first supporting structure 30a. For example, the first supporting structure 30a is a bar-like member that has a male screw structure on one end thereof and has a hexagonal prism shape near the center thereof. Further, the second supporting structure 30b is a member having a female screw structure corresponding to the male screw thread of the first supporting structure 30a and is fixed to the magnetostatic field magnet 101 by a fixing device 32 (a bolt or the like). Further, the third supporting structure 30c is a member that rotatably supports the first supporting structure 30a and is fixed to the bore tube 13 via the vibration-isolating member 31. The vibration-isolating member 31 is, for example, formed by using rubber or an elastic foam material and is configured to reduce the vibration of the gradient coil 103.

In this situation, the male screw thread of the first supporting structure 30a is engaged with the female screw thread of the second supporting structure 30b (a lead screw structure). Further, the other end of the first supporting structure 30a having no male screw structure is rotatably inserted into the third supporting structure 30c. With these arrangements, for example, a worker is able to adjust the length of the entirety of the supporting structure 30 to any arbitrary length, by rotating the hexagonal prism part of the first supporting structure 30a with a tool such as a wrench.

Further, as illustrated in FIG. 7, for example, eight supporting structures 30 (supporting structures 301, 302, 303, 304, 305, 306, 307, and 308) are installed in a radial formation surrounding the bore tube 13. With these arrangements, a worker is able to fix the bore tube 13 in an arbitrary position, by adjusting the length of each of the supporting structures 30 to an arbitrary length.

As explained above, in the MRI apparatus 100 according to the first embodiment, the supporting structures 30 are able to fix the bore tube 13 in an arbitrary position. Consequently, the MRI apparatus 100 is configured so that it is possible to keep the length E constant at an arbitrary length.

Further, in the MRI apparatus 100, the supporting structures 30 support a large part of the weight of the bore tube 13. For this reason, the MRI apparatus 100 is configured so that the weight of the bore tube 13 applied on the vacuum sealing members 20 is reduced. Consequently, it is possible to maintain the vacuum sealing capability of the vacuum sealing members 20 and to reduce the solid-propagated sound that propagates by using the vacuum sealing members 20 themselves as a medium.

Further, because the MRI apparatus 100 includes the vibration-isolating members 31, it is possible to inhibit the vibration of the gradient coil 103. Further, because the vibration is inhibited, the MRI apparatus 100 is configured so that it is possible to reinforce the vacuum sealing capability of the vacuum sealing members 20 and to delay deterioration of the vacuum sealing members 20.

The configuration illustrated in FIG. 6 is merely an example. For instance, the third supporting structure 30c may be integrally formed with the bore tube 13. In that situation, the bore tube 13 has a hole that rotatably supports the first supporting structure 30a. In other words, it is sufficient if the MRI apparatus 100 includes at least the first supporting structure 30a and the second supporting structure 30b, as elements of each of the supporting structures 30.

Further, for example, the vibration-isolating member 31 does not necessarily have to be installed between the third supporting structure 30c and the bore tube 13. For example, the vibration-isolating member 31 may be installed between the first supporting structure 30a and the third supporting structure 30c or may be installed between the second supporting structure 30b and the magnetostatic field magnet 101.

Further, the configuration illustrated in FIG. 7 is merely an example. For instance, the number of supporting structures 30 does not necessarily have to be eight. In other words, as long as it is possible to fix the bore tube 13 in an arbitrary position, it is acceptable to install the supporting structures 30 in any arbitrary quantity.

The Sound-Blocking Lids 40

A structure of the sound-blocking lids 40 will be explained, with reference to FIGS. 6 and 7. The sound-blocking lid 40 illustrated in FIG. 6 is a plate-like member formed by using Fiber Reinforced Plastic (FRP) or the like. A vibration-isolating member 41 formed by using rubber or an elastic foam material is provided between the sound-blocking lid 40 and the gradient coil 103.

As illustrated in FIG. 7, for example, eight pieces (sound-blocking lid pieces 40a, 40b, 40c, 40d, 40e, 40f, 40g, and 40h) structuring the sound-blocking lid 40 are installed so as to close the space formed between the magnetostatic field magnet 101 and the gradient coil 103. Each of the sound-blocking lid pieces 40a to 40h is a plate-like member formed to have an arc shape. In this situation, the reason why the sound-blocking lid 40 is installed while being separated as the eight plate-like pieces is that the sound-blocking lid 40 is installed after the bore tube 13 is supported on the magnetostatic field magnet 101 by the supporting structures 301 to 308. In other words, the sound-blocking lid pieces 40a to 40h are inserted through the intervals between the supporting structures 301 to 308 that have been installed between the magnetostatic field magnet 101 and the bore tube 13. Further, the sound-blocking lid pieces 40a to 40h hermetically seal the space formed between the magnetostatic field magnet 101 and the gradient coil 103 as a result of being shifted around so as to cover the entire area on the end faces of the magnetostatic field magnet 101 and the gradient coil 103. In this situation, the space formed between the magnetostatic field magnet 101 and the gradient coil 103 is kept at the atmospheric pressure.

As explained above, in the MRI apparatus 100, the sound-blocking lids 40 close the space formed between the magnetostatic field magnet 101 and the gradient coil 103. In this situation, the impact made on the patient P by the air-propagated sound (the outside air-propagated sound) leaking from this space is small, as mentioned above. Thus, the MRI apparatus 100 is configured so that it is possible to reduce the outside air-propagated sound by using the simple configuration.

Further, in the MRI apparatus 100, the pieces structuring each of the sound-blocking lids 40 are installed by being inserted through the intervals between the eight supporting structures 301 to 308. Consequently, it is easy to assemble the sound-blocking lids 40.

Although FIG. 7 illustrates an example in which the space formed between the magnetostatic field magnet 101 and the gradient coil 103 is hermetically sealed; however, the space does not necessarily have to be hermetically sealed. For example, the sound-blocking lid pieces 40a to 40h may be formed in any size that can be accommodated in the intervals between the eight supporting structures 301 to 308. Further, the sound-blocking lid pieces 40a to 40h are arranged in the intervals between the supporting structures 301 to 308. In that situation, there are gaps between the sound-blocking lid pieces 40a to 40h. Further, the number of sound-blocking lid pieces structuring each of the sound-blocking lids 40 does not necessarily have to be eight. For example, each of the sound-blocking lids 40 may be provided in pieces in any arbitrary quantity, as long as it is possible to reduce the outside air-propagated sound. Also, the sound-blocking lids 40 do not necessarily have to be installed, if the outside air-propagated sound is sufficiently reduced.

Further, the sound-blocking lids 40 do not necessarily have to be formed by using FRP. For example, the sound-blocking lids 40 themselves may be formed by using a vibration-isolating material such as rubber or an elastic foam material. For example, sealing members having the same configurations as those of the vacuum sealing members 20 may be arranged so as to close the space (the second space) formed between the magnetostatic field magnet 101 and the gradient coil 103. In that situation, the second space may be or may not be hermetically sealed. When the second space is not hermetically sealed, for example, the sealing members do not necessarily have to be hollow and do not necessarily have to have the hole 21 formed therein, unlike the vacuum sealing members 20. As explained herein, even if the second space is not hermetically sealed, it is possible to effectively reduce the outside air-propagated sound only by closing the second space by using the sealing members formed with a foam material. In that situation, the vibration-isolating members 41 do not necessarily have to be installed.

Installation of the Couch Rail 14

Installation of the couch rail 14 will be explained, with reference to FIG. 2. As illustrated in FIG. 2, the couch rail 14 is supported on the magnetostatic field magnet 101 by the couch rail supporting unit 15. In this situation, the couch rail supporting unit 15 is structured so as not to be in contact with the bore tube 13. The couch rail 14 has a sufficient level of rigidity so as not to be deformed by at least the weight of the patient P and may be formed by using, for example, FRP.

As explained above, in the MRI apparatus 100, the couch rail 14 is supported on the magnetostatic field magnet 101. Accordingly, the MRI apparatus 100 is configured so that, even when the couchtop 105a is inserted into the bore, the weight of the patient P is not applied on the vacuum sealing members 20. Consequently, the configuration contributes to maintaining the vacuum sealing capability of the vacuum sealing members 20. In addition, it is also possible to inhibit the solid-propagated sound that uses the vacuum sealing members 20 as a medium.

As explained above, the MRI apparatus 100 according to the first embodiment is configured so that it is possible to reduce the noise by using the simple configuration. In other words, in the MRI apparatus 100 according to the first embodiment, the first space is configured to be kept in a vacuum state while a second space is configured to be kept in a state not being a vacuum.

Other Embodiments

The first embodiment has thus been explained. It is possible to carry out the disclosure herein in various modes other than those described in the first embodiment.

Supporting the Couch Rail 14 on the Floor

For example, in the embodiments described above, the example is explained in which the couch rail 14 is supported on the magnetostatic field magnet 101. However, possible embodiments are not limited to this example. For instance, the couch rail 14 may be supported on the floor.

Figure 8:
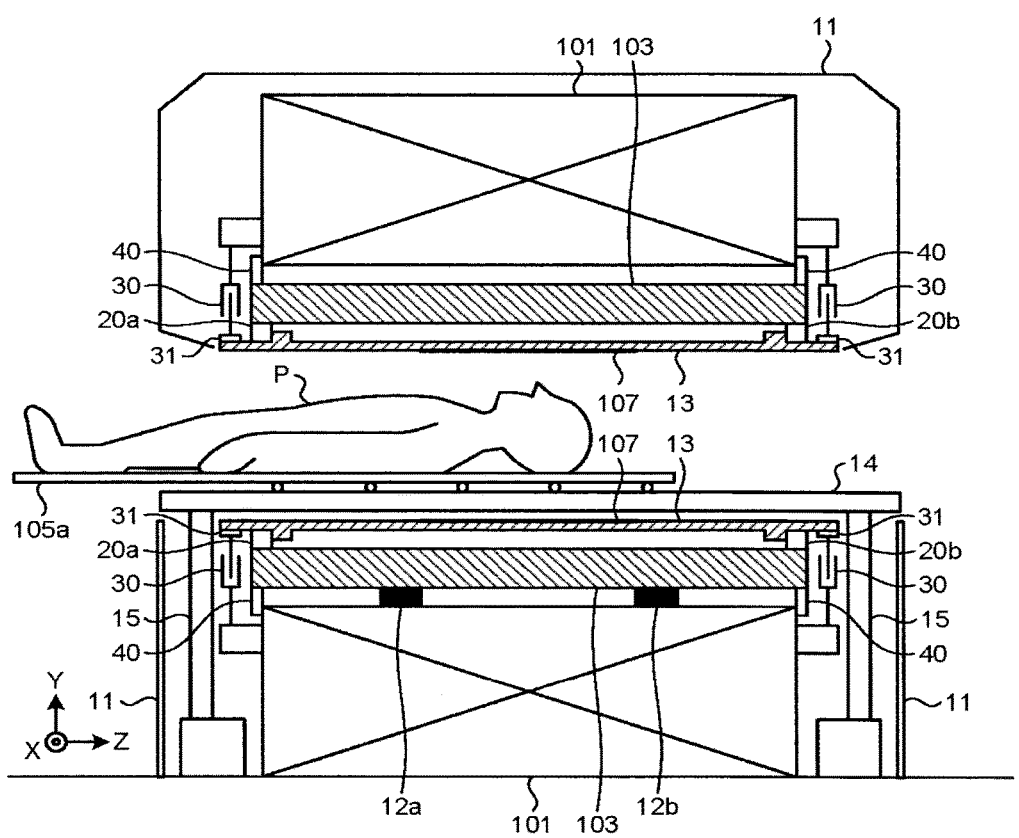
FIG. 8 is a drawing for explaining an internal structure of a gantry of an MRI apparatus according to another embodiment.

FIG. 8 is a drawing for explaining an internal structure of a gantry of an MRI apparatus according to another embodiment. In the example illustrated in FIG. 8, the couch rail 14 is supported on the floor by the couch rail supporting unit 15. By supporting the couch rail 14 on the floor in this manner, the MRI apparatus 100 is configured so that it is possible to maintain the vacuum sealing capability of the vacuum sealing members 20 and to reduce the solid-propagated sound that propagates by using the vacuum sealing members 20 themselves as a medium.

Supporting the Bore Tube 13 on the Floor

Further, for instance, in the embodiments described above, the example is explained in which the bore tube 13 is supported on the magnetostatic field magnet 101; however, possible embodiments are not limited to this example. For instance, the bore tube 13 may be supported on the floor.

Figure 9:
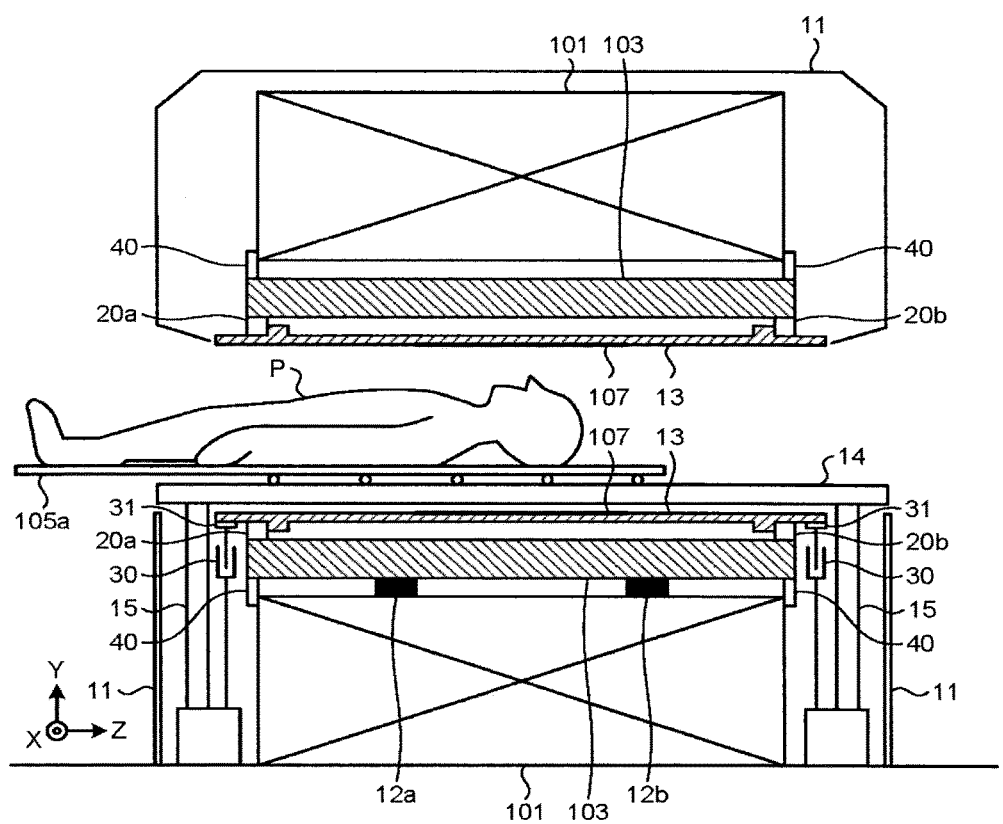
FIG. 9 is a drawing for explaining an internal structure of a gantry of an MRI apparatus according to yet another embodiment.

FIG. 9 is a drawing for explaining an internal structure of a gantry of an MRI apparatus according to yet another embodiment. In the example illustrated in FIG. 9, the bore tube 13 is supported on the floor by the supporting structures 30. By supporting the bore tube 13 on the floor in this manner, the MRI apparatus 100 is configured so that it is possible to maintain the vacuum sealing capability of the vacuum sealing members 20 and to reduce the solid-propagated sound that propagates by using the vacuum sealing members 20 themselves as a medium.

Position of the Projection

Further, for instance, in the embodiments described above, the example is explained in which the projection 13a is provided on the outer circumferential surface of the bore tube 13; however, possible embodiments are not limited to this example. For instance, the projection 13a may be provided on the inner circumferential surface of the gradient coil 103. Alternatively, the projection 13a may be provided on the outer circumferential surface of the bore tube 13 and on the inner circumferential surface of the gradient coil 103.

Bringing the Space (The Second Space) Formed Between the Gradient Coil 103 and the Magnetostatic Field Magnet 101 into a Vacuum State Further, for instance, in the embodiments described above, the example is explained in which the space formed between the gradient coil 103 and the bore tube 13 is hermetically sealed and brought into a vacuum state; however, possible embodiments are not limited to this example. For instance, in addition to the space formed between the gradient coil 103 and the bore tube 13, the space formed between the gradient coil 103 and the magnetostatic field magnet 101 may also be hermetically sealed and brought into a vacuum state.

In that situation, for example, the projection 13a is provided on at least one selected from between the outer circumferential surface of the gradient coil 103 and the inner circumferential surface of the magnetostatic field magnet 101. Further, as being inserted from the two ends in the axial direction, the vacuum sealing members 20 hermetically seal the space formed between the gradient coil 103 and the magnetostatic field magnet 101. Further, as a result of the vacuum pump 111 evacuating the air from the inside of the space, the space is brought into the vacuum state.

As explained above, because the space formed between the gradient coil 103 and the magnetostatic field magnet 101 is brought into the vacuum state, the MRI apparatus 100 is configured so that it is possible to efficiently block the outside air-propagated sound.

Figure 10:
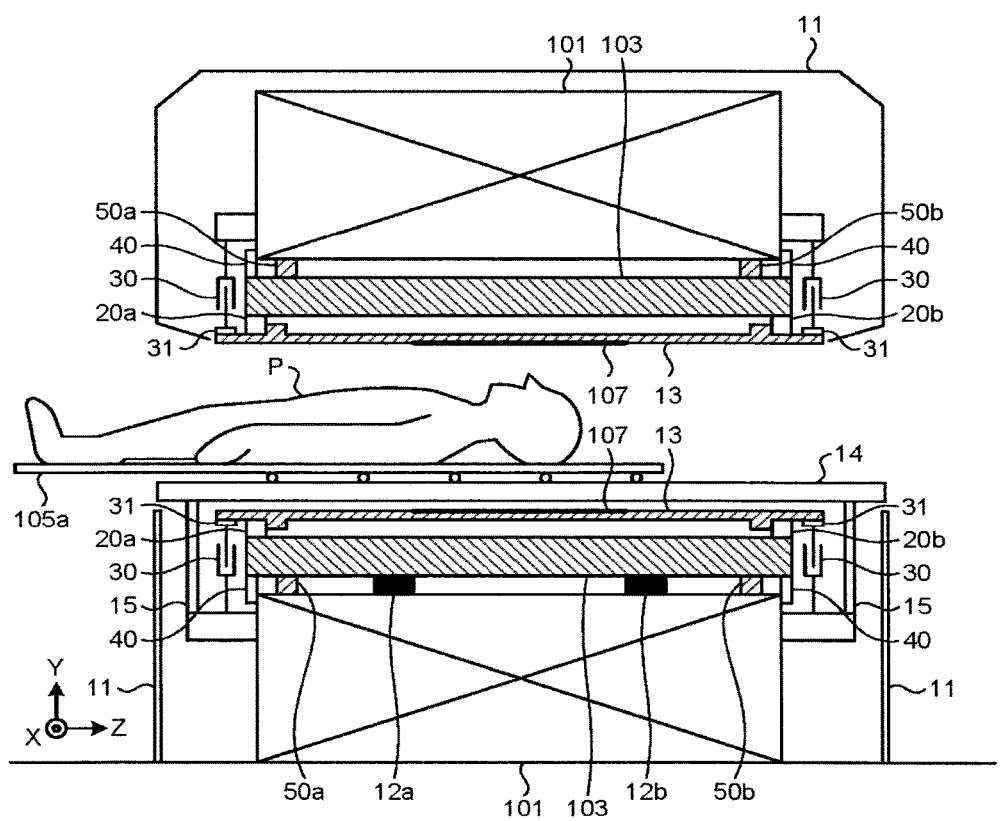
FIG. 10 is a drawing for explaining an internal structure of a gantry of an MRI apparatus according to yet another embodiment.
Figure 11:
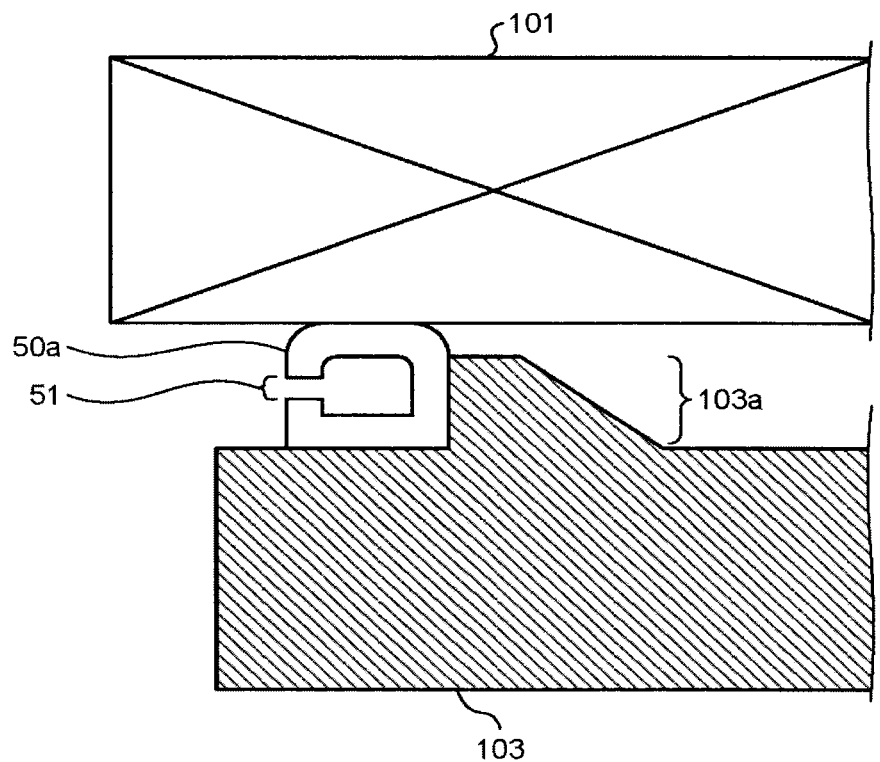
FIG. 11 is a drawing for explaining a structure of vacuum sealing members according to the embodiment.

A configuration used when the second space is brought into a vacuum state will be explained with reference to FIGS. 10 and 11. FIG. 10 is a drawing for explaining an internal structure of a gantry of an MRI apparatus according to yet another embodiment. FIG. 10 is a cross-sectional view on a y-z plane passing through the central axis of the magnetostatic field magnet 101. FIG. 11 is a drawing for explaining a structure of vacuum sealing members 50a and 50b according to the embodiment. FIG. 11 is a cross-sectional view obtained when the vacuum sealing member 50a is inserted into the position between the gradient coil 103 and the magnetostatic field magnet 101. Because the vacuum sealing members 50a and 50b have the same configuration as each other, the vacuum sealing member 50a will be explained, with reference to FIG. 11.

As illustrated in FIG. 10, for example, the vacuum sealing members 50a and 50b are each arranged so as to hermetically seal the space (the second space) formed between the gradient coil 103 and the magnetostatic field magnet 101. Except for having larger diameters than those of the vacuum sealing members 20a and 20b, the vacuum sealing members 50a and 50b each have the same structure as those of the vacuum sealing members 20a and 20b. For example, the vacuum sealing members 50a and 50b are each an elastic member obtained by forming a foam material such as chloroprene into an annular shape. Further, the second space hermetically sealed by the vacuum sealing members 50a and 50b is brought into a vacuum state by the vacuum pump 111. Except for including the vacuum sealing members 50a and 50b, the MRI apparatus 100 illustrated in FIG. 10 has the same configuration as the configuration illustrated in FIG. 2.

As illustrated in FIG. 11, the vacuum sealing member 50a is inserted into the space formed between the gradient coil 103 and the magnetostatic field magnet 101 while being squashed. With this arrangement, even if the gradient coil 103 vibrates, because the vacuum sealing member 50a changes the form thereof so as to conform to the vibration (shape conformability), it is possible to maintain the hermetically-sealed space.

Further, the gradient coil 103 has a projection 103a formed on the outer circumferential surface thereof. The projection 103a is formed in the circumferential direction on the outer circumferential surface of the gradient coil 103 and is configured to fix the vacuum sealing member 50a in the vicinity of the end part in terms of the axial direction. With these arrangements, it is possible to arrange the vacuum sealing member 50a so as not to be sucked, even when the second space is brought into a vacuum state. Further, the distance between the projection 103a and the magnetostatic field magnet 101 may be changed to any arbitrary length. For example, the distance between the projection 103a and the magnetostatic field magnet 101 may be increased so long as the vacuum sealing member 50a is not sucked into the second space. Conversely, the distance between the projection 103a and the magnetostatic field magnet 101 may be decreased so long as the projection 103a and the magnetostatic field magnet 101 do not collide with each other due to vibration of the gradient coil 103. Alternatively, the projection 103a may be formed on the magnetostatic field magnet 101. For example, the projection 103a may be formed in the circumferential direction on the inner circumferential surface of the magnetostatic field magnet 101.

Further, the vacuum sealing member 50a has an annular-shaped hollow on the inside thereof, and also, has formed therein a hole 51 that reaches the hollow, on the plane positioned opposite the plane positioned on the hermetically-sealed space side. The hole 51 allows air to flow into the hollow of the vacuum sealing member 20. With these arrangements, as a result of the atmospheric pressure being applied to the surface of the hollow of the vacuum sealing member 20, it is possible to improve the sealing capability as well as to improve the shape conformability. In this situation, like the hole 21, the hole 51 may have an arbitrary shape and may be provided in an arbitrary quantity.

As explained above, in the MRI apparatus 100 in the other embodiment, the vacuum sealing members 50a and 50b hermetically seal the second space. In other words, the first space and second space are configured to be kept in a vacuum state. As a result, the MRI apparatus 100 according to the other embodiment is configured so that it is possible to reduce the air-propagated sound on the outside of the gradient coil 103 by using the simple configuration.

Attaching and Detaching the Vacuum Pump 111

Further, for instance, in the embodiments described above, the example is explained in which the vacuum pump 111 is always provided for the MRI apparatus 100; however, possible embodiments are not limited to this example. For instance, the vacuum pump 111 may be installed when bringing the space formed between the gradient coil 103 and the bore tube 13 or the space formed between the gradient coil 103 and the magnetostatic field magnet 101 into a vacuum state, so that the vacuum pump 111 is removed from the MRI apparatus 100 while the vacuum state is maintained. In other words, the vacuum pump 111 may be attached and detached as necessary.

According to at least one aspect of the embodiments described above, it is possible to reduce the noise by using the simple configuration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A magnetic resonance imaging apparatus comprising:
a magnetostatic field magnet formed to have a cylindrical shape;
a gradient coil formed to have a cylindrical shape, on an inside of the magnetostatic field magnet;
a bore tube formed to have a cylindrical shape, on an inside of the gradient coil, and
a hermetically-sealing member configured to hermetically seal a space between the gradient coil and the bore tube, wherein
the hermetically-sealing member is an annular-shaped member that has a hollow inside and has a hole formed therein through which air is drawn into the hollow.

2. The magnetic resonance imaging apparatus according to claim 1, wherein the hermetically-sealing member is formed by using a foam material having a closed-cell foam structure.

3. The magnetic resonance imaging apparatus according to claim 2, wherein sizes of cells in the closed-cell foam structure are arranged in such a manner that the closer a cell is positioned to a surface of the hermetically-sealing member, the smaller the cell is.

4. The magnetic resonance imaging apparatus according to claim 1, wherein the bore tube has a projection formed on a surface thereof that is in contact with the hermetically-sealing member.

5. The magnetic resonance imaging apparatus according to claim 4, wherein a distance between the projection and the gradient coil is equal to or shorter than a half of a distance between the bore tube and the gradient coil.

6. The magnetic resonance imaging apparatus according to claim 1, wherein the gradient coil has a projection formed on a surface thereof positioned on a side that is in contact with the hermetically-sealing member.

7. The magnetic resonance imaging apparatus according to claim 1, further comprising: a supporting structure configured to support the bore tube on the magnetostatic field magnet.

8. The magnetic resonance imaging apparatus according to claim 7, wherein the supporting structure includes a first supporting structure having a male screw thread and a second supporting structure having a female screw thread corresponding to the male screw thread.

9. The magnetic resonance imaging apparatus according to claim 1, wherein the bore tube is supported on a floor.

10. The magnetic resonance imaging apparatus according to claim 1, wherein a rail for a couch on which a patient is placed is supported on either the magnetostatic field magnet or a floor.

11. The magnetic resonance imaging apparatus according to claim 1, further comprising: a lid configured to close a space formed between the magnetostatic field magnet and the gradient coil while being provided on at least one end face of the magnetostatic field magnet.

12. The magnetic resonance imaging apparatus according to claim 11, wherein the lid has a member provided on a face thereof that is in contact with either the magnetostatic field magnet or the gradient coil, the member being formed by using either a rubber material or an elastic foam material.

13. The magnetic resonance imaging apparatus according to claim 11, wherein the lid is configured with a plurality of plate-like members each having an arc shape, and
the space formed between the magnetostatic field magnet and the gradient coil is closed by arranging the plurality of plate-like members in an annular formation.

14. The magnetic resonance imaging apparatus according to claim 1, further comprising:
a vacuum pump configured to bring a first space between the gradient coil and the bore tube into a vacuum state while a second space between the gradient coil and the magnetostatic field magnet is kept in a state not being a vacuum.

15. The magnetic resonance imaging apparatus according to claim 1, wherein the space and another space between the gradient coil and the magnetostatic field magnet are configured to be kept in a vacuum state.

16. The magnetic resonance imaging apparatus according to claim 1, wherein a first space between the gradient coil and the bore tube is configured to be kept in a vacuum state while a second space between the gradient coil and the magnetostatic field magnet is configured to be kept in a state not being a vacuum.

* * * * *